(12) United States Patent
Wilkinson et al.

(10) Patent No.: US 6,235,010 B1
(45) Date of Patent: May 22, 2001

(54) CLOSED SYSTEM SPECIMEN COLLECTION CONTAINER

(75) Inventors: Bradley M. Wilkinson, North Haledon; Robert S. Golabek, Jr., Towaco, both of NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/369,994

(22) Filed: Aug. 6, 1999

(51) Int. Cl.[7] .................................................. A61B 19/00
(52) U.S. Cl. ......................... 604/356; 600/573; 604/317; 604/324
(58) Field of Search .................... 4/144.1–144.4; 600/573; 383/80; 604/73, 317–324, 327–331, 356; 422/55–59; D24/121

(56) References Cited

U.S. PATENT DOCUMENTS

| | | | |
|---|---|---|---|
| 3,750,647 | 8/1973 | Gleason et al. | 128/2 F |
| 4,106,490 | 8/1978 | Spilman et al. | 128/2 F |
| 4,116,066 | 9/1978 | Mehl et al. | 73/421 R |
| 4,121,306 | 10/1978 | Bringman et al. | 4/144.2 |
| 4,252,132 * | 2/1981 | Kuntz | 604/356 |
| 4,258,032 | 3/1981 | Mehl | 424/148 |
| 4,300,404 | 11/1981 | Mehl et al. | 73/863.52 |
| 4,335,730 | 6/1982 | Griffin | 128/760 |
| 4,393,881 | 7/1983 | Shah | 128/760 |
| 4,492,258 | 1/1985 | Lichtenstein et al. | 141/1 |
| 4,761,379 | 8/1988 | Williams et al. | 435/296 |
| 4,769,215 | 9/1988 | Ehrenkranz | 422/58 |
| 4,895,167 | 1/1990 | Guala | 128/760 |
| 5,069,878 | 12/1991 | Ehrenkranz | 422/61 |
| 5,147,342 | 9/1992 | Kane et al. | 604/356 |
| 5,251,639 | 10/1993 | Rentsch | 128/761 |
| 5,422,076 | 6/1995 | Jones | 422/102 |
| 5,569,225 | 10/1996 | Fleury | 604/323 |
| 5,797,855 | 8/1998 | Hazard et al. | 600/513 |
| 5,849,505 | 12/1998 | Guirguis | 435/7.2 |
| 5,893,176 | 4/1999 | Magiera et al. | 4/144.4 |
| 5,894,607 | 4/1999 | Van Den Burg | 4/144.2 |
| 5,894,608 * | 4/1999 | Birbara | 4/144.3 |
| 5,897,840 | 4/1999 | Owens, Jr. et al. | 422/102 |

* cited by examiner

Primary Examiner—Anhtuan T. Nguyen
Assistant Examiner—Michael M. Thompson
(74) Attorney, Agent, or Firm—Nanette S. Thomas; Keith J. McWha

(57) ABSTRACT

This invention relates to a closed system specimen collection container. The collection container is designed to collect, transport and transfer the liquid specimen into a non-evacuated tube through an integrated valve component. This device has no sharp needles and utilizes a blunt cannula component on a test tube. The operation of the device consists of the steps of collecting a specimen into the container and attaching a cap in permanent locking and leak resistant attachment. The cap may be a snap-on or threaded lock. The specimen may then be immediately transported to a laboratory in the container where the specimen can be transferred into a tube for analysis. Alternatively, the specimen may then be immediately transferred into a non-evacuated tube through the integrated valve by a passive means. This technique is accomplished by inserting the blunt cannula attached to the tube into the bottom of the container and interfacing with the integrated valve component. The valve is pierced by the blunt cannula on the tube allowing passive transfer of the specimen without the user coming in contact with the liquid. Gravity allows liquid to transfer automatically. The filled test tube is then pulled off of the container and a second tube may be filled at that time if desired. The container may then be discarded for proper disposal. The integrated valve is a self-sealing valve which allows the user to obtain multiple tube samples without the risk of leaks or spills from the container.

9 Claims, 7 Drawing Sheets

CLOSED SYSTEM SPECIMEN COLLECTION CONTAINER

BACKGROUND OF THE INVENTION

1. Field of the Invention

The invention relates generally to an apparatus for collecting and transferring biological fluids. More particularly, the present invention relates to an apparatus for collecting and transferring a urine specimen in conjunction with a collection tube.

2. Description of Prior Art

Biological fluids are collected periodically for laboratory analysis. Laboratory equipment that performs the analysis may only accept biological fluids stored in a test tube. However, a test tube is too small for the convenient collection of many biological fluids, such as urine. As a result, specimens often are collected in a fairly large container with a widely open top. After collection of the fluid in the container, the container is delivered to a medical technician. The medical technician then transfers a portion of the fluid into a test tube that is sealed and transported to a laboratory for analysis. The transfer of biological fluid from the collection container to the test tube is an unpleasant task that creates the risk of contaminating the specimen or exposing the medical technician to potentially harmful pathogens in the specimen.

Some biological fluids such as blood are collected with assemblies that include a vacuum tube and a double-ended needle cannula. One end of the needle cannula is placed in communication with the biological fluid. The opposite end of the needle cannula is urged through a vacuum seal into the vacuum tube. Low pressure within the vacuum tube generates a flow of the bodily fluid through the needle cannula and into the tube. Such vacuum tubes are very convenient and efficient for collecting blood samples. However, for urine specimen collection, vacuum tubes are not very useful because vacuum tubes only have a limited shelf life due to a gradual migration of gas molecules through the walls of the tube. Additionally, sharps or pointed cannula require careful shielding to avoid potential skin punctures.

In urine collection, some prior art collection containers have a test tube that is attached. In this prior art device, a portion of the urine specimen in the container is automatically transferred to the test tube. The test tube then may be separated from the container, sealed and shipped to a laboratory for analysis. However, these prior art assemblies can lead to leakage during the initial collection of the specimen or after the separation of the test tube from the collection container. Additionally, control of the volume of the specimen in the test tube may vary from sample to sample. A means for controlling the volume in each specimen sample taken is needed to assure accurate results in the subsequent laboratory analysis. Also, the use of a non-sharp or blunt cannula in the transfer of the specimen from the collection container to the test tube is preferred to avoid potential skin puncturing of the medical technician. Finally, a collection container designed to avoid contact with the user to prevent contamination of the specimen is desired. Prior art assemblies of collection containers can come into contact with the user's hands during collection which contaminate the specimen in the collection container. Finally, there is a need for a collection container to use a non-evacuated vacuum tube to avoid the potential limited shelf life of the vacuum tube.

SUMMARY OF THE INVENTION

The present invention alleviates in great part the drawbacks associated with prior art specimen collection containers. Provided is a container that allows transport of the specimen to a laboratory for analysis and minimizes the risk of spills or leaks. The present invention preserves non-contamination during collection and transfer between the collection container and collection tube. This transfer can be done either in the physician's office or at a laboratory.

The invention is directed to a closed system specimen collection container. The container has a bottom, an open top, and side walls extending from the bottom to the top. The bottom has a circular top surface and a bottom surface. The top surface is inclined and has an aperture located at the lowest gravitational point on the top surface. The aperture is non-eccentric to the top surface.

The container also includes an integrated valve that protrudes from the bottom surface. It is offset from the center point of the bottom. The valve is in fluid communication with the aperture and allows multiple sampling such that the valve is open when it is punctured by a piercing member and the valve is closed when the puncture is removed. A lid is also included in the collection container. The lid is disposed around the open top and has a recessed area containing a vent. The vent allows air to permeate the container. The vent further includes an air-permeable membrane that provides for the specimen to remain within the container. The vent on the lid is offset from the center point of the lid. This geometry allows maximum air permeation during collection.

The collection container further includes a circular extension portion connected to the bottom and extending approximately downward. The circular extension portion has a substantial planar bottom for the container to stand unassisted on a flat surface. The circular extension portion is further characterized by having a hemispherical recess that allows access to the valve. The bottom is further characterized by having an annular protective flap surrounding the valve for reducing splatter when the valve is pierced.

The side walls include at least one external protrusion and the lid includes at least one internal protrusion such that when the lid is connected by the internal protrusion to the external protrusion, a permanent and leak-resistant connection is formed between the lid and the side walls. A crimp area on the lid provides the permanent and leak-resistant connection.

The top surface of the bottom of the container has grooves symmetrically surrounding the aperture. The function of the grooves is to facilitate flow of the specimen toward the aperture. The valve includes a conical inlet for providing audible and tactile confirmation of the opening when the valve is pierced. The side walls and the lid are further characterized by comprising an array of ribs that allows gripping the lid during locking of the lid on the side walls.

The specimen collection container further includes a test tube. The test tube has a closed bottom, an open top and cylindrical side walls extending therebetween. A stopper is attached to the open top. The stopper has a piercing member for attaching the test tube to the valve such that the container is in fluid communication with the test tube. The valve is preferably made of an elastomeric material and the container and circular extension portion are preferably a unitary structure.

DETAILED DESCRIPTION

Figure 1:
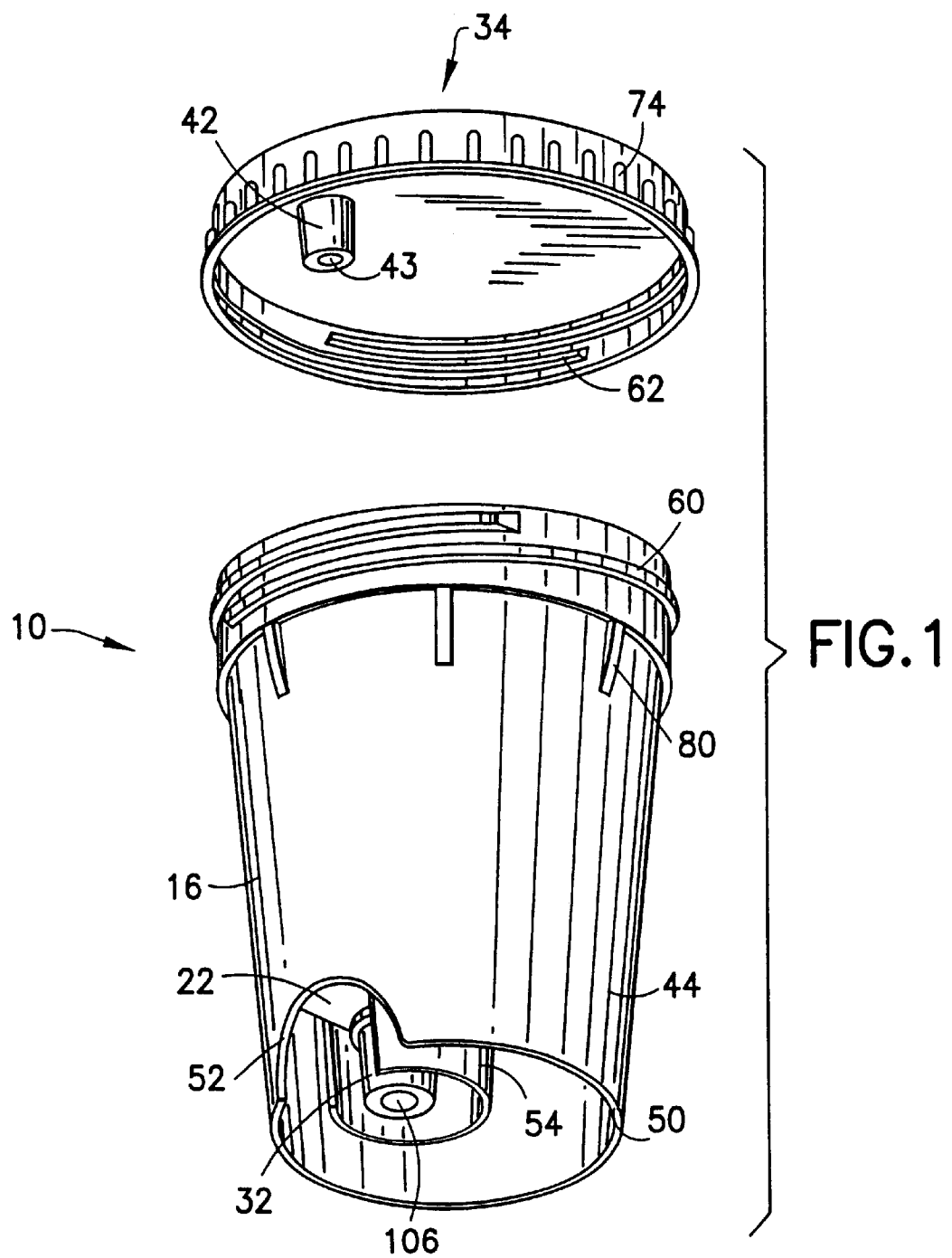
FIG. 1 is an exploded perspective view of the closed system specimen collection container in accordance with the subject invention.

A closed system specimen collection container in accordance with the subject invention is identified generally by numeral 10 as shown in FIGS. 1–9. A closed system specimen collection container includes a bottom 12, an open top 14, and side walls 16 extending from bottom 12 to open top 14. Bottom 12 has a circular top surface 20 and a bottom surface 22. Top surface 20 is inclined and has an aperture 24 therethrough located at a point 30 that is the lowest gravitational point on top surface 20.

Aperture 24 is further characterized as being non-eccentric to top surface 20. The function of this geometry is to allow the maximum comfort and accessibility in attaching the transfer container to integrated valve 30 of collection container 10.

Figure 2:
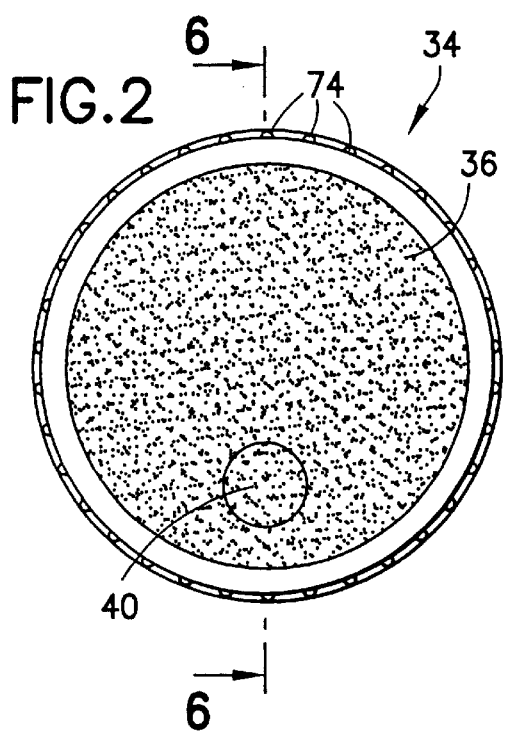
FIG. 2 is an assembled top plane view of the container shown in FIG. 1.
Figure 2A:
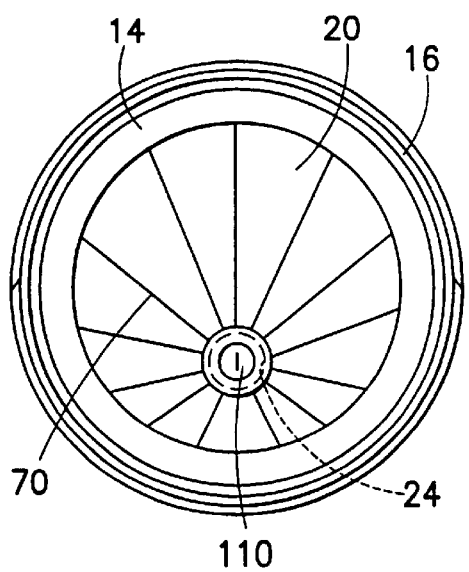
FIG. 2A is a top plane view of the container in FIG. 1 without the lid.

Circular top surface 20 is further characterized by having a plurality of grooves 70 symmetrically surrounding aperture 24. The function of grooves 70 is to facilitate flow of the specimen toward aperture 24 as shown in FIG. 2A.

Figure 5:
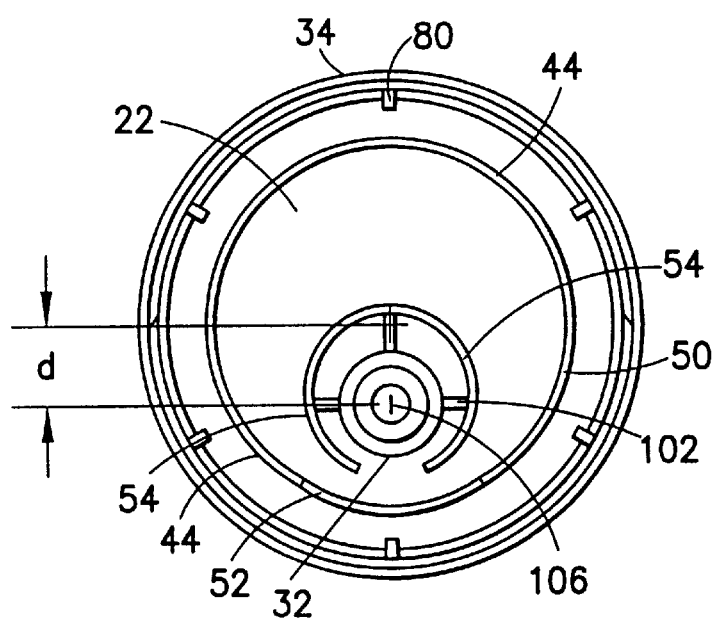
FIG. 5 is a bottom view of the collection container shown in FIG. 1.

Container 10 further includes an integrated valve 32 protruding distally from bottom surface 22 and offset from the center point of bottom surface 22 by a distance "d" as shown in FIG. 5. Valve 32 is in fluid communication with aperture 24 and is inserted in aperture 24. Valve 32 is further characterized by allowing multiple specimen sampling such that valve 32 is opened when the valve is punctured and the valve is closed when the puncture is removed. This self-sealing property that valve 32 contains allows transfer of the specimen from the closed system specimen collection container 10 without any leakage of the specimen from collection container 10. Valve 32 can be in any position on a collection container 10 and still provide this self-sealing property.

Figure 6:
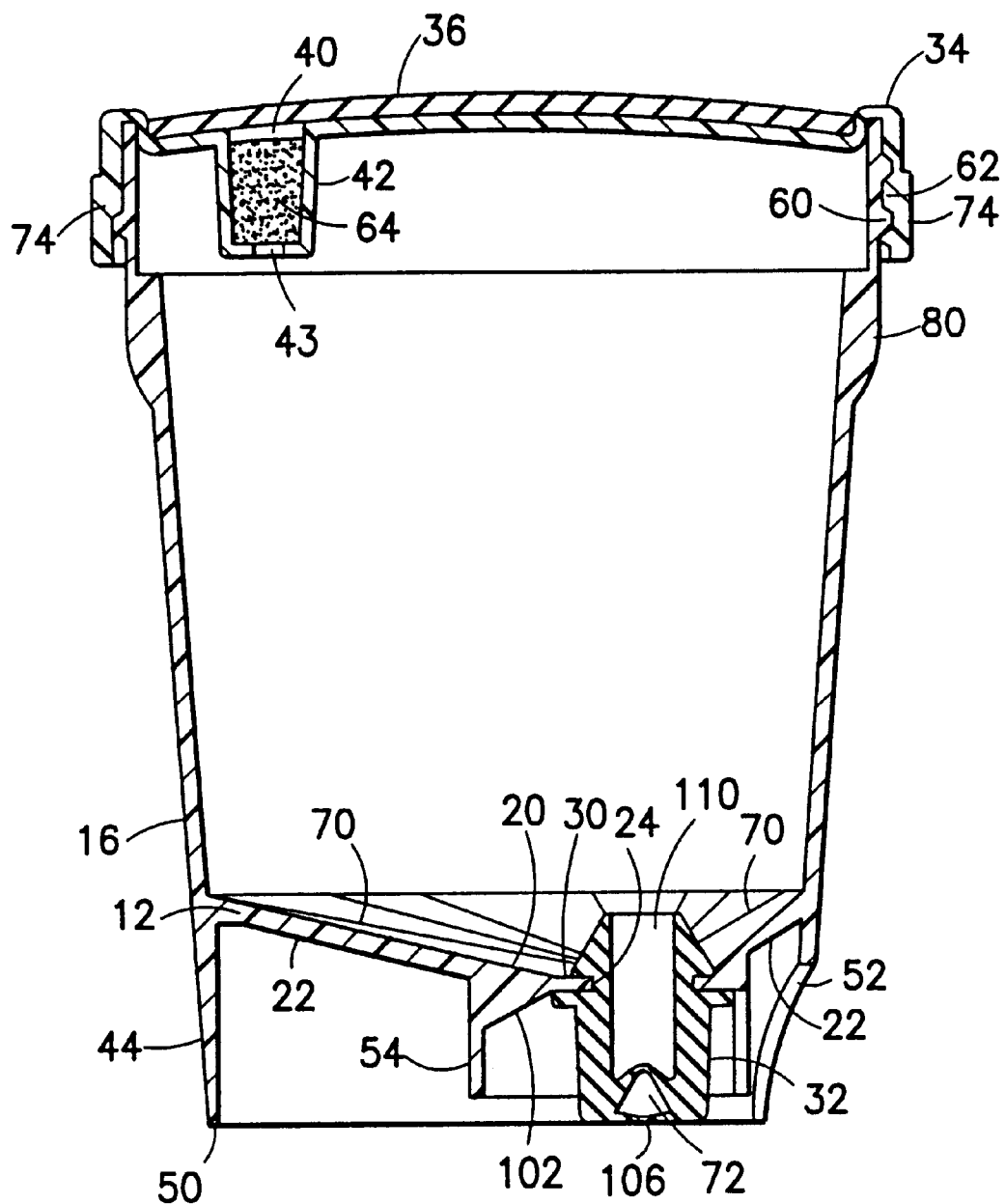
FIG. 6 is a cross-sectional view taken along lines 6—6 in FIG. 2.

Collection container 10 further includes a lid 34 disposed around open top 14. Lid 34 has a recessed area 40 forming a vent 42. Vent 42 allows air to permeate through container 10. Vent 42 is further characterized, as shown in FIG. 6, by having a vent hole 43 centrally located on the bottom of vent 42. Recessed area 40 is filled with an air-permeable membrane 64. Air-permeable membrane 64 is in fluid communication with vent hole 43. Air-permeable membrane 64 is disposed inside vent 42. Membrane 64 prevents the escape of the specimen within the container and allows air to pass through vent hole 43 to facilitate multiple transfers of the specimen through valve 32 when valve 32 is pierced. Thus, membrane 64 allows air to permeate but prevents liquid to permeate through it. By having membrane 64 inside vent 42, venting and thus transferring of the specimen from container 10 is controlled based on the size and density of the membrane. Membrane 64 can be easily changed by simple, manual replacement. Thus, the speed of transferring the specimen is easily altered.

Lid 34 as shown in FIG. 6 contains a lid cover 36. Lid cover 36 secures membrane 64 in vent 42. Lid cover 36 allows air to permeate but would not allow fluid. Thus, the main function of lid cover 36 is to prevent membrane 64 from moving. Lid cover 36 is centrally disposed on lid 34. Preferably, lid cover 36 is heat sealed on lid 34. Lid cover 36 can be attached to lid 34 using various methods. Such methods include ultrasonic welding, adhesive bonding, mechanical fasteners, snap-fittings, and heat welding.

Figure 7:
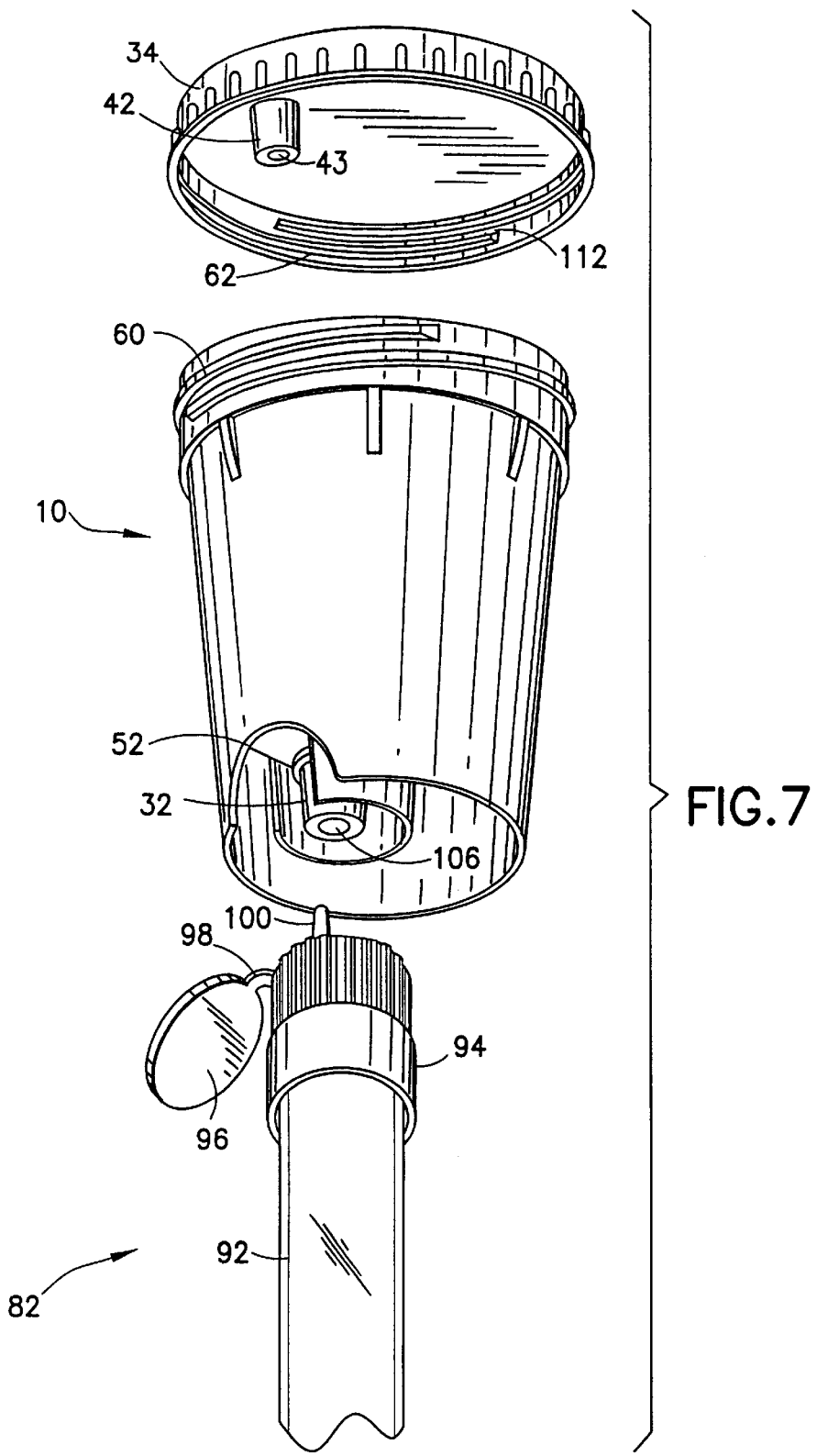
FIG. 7 is an exploded perspective view of the specimen collection container and a test tube assembly mounted to the collection container.

As shown in FIGS. 1 and 7, vent 42 is further characterized by being offset on lid 34 from the center point of the lid 34. The purpose of this geometry is to maximize the amount of air permeated through vent 42 by aligning vent 42 with a high gravitational point on surface 20.

Container 10 is further characterized having a circular extension portion 44 connected to bottom 12 and extending approximately downward. Circular extension portion 44 has a substantially planar bottom 50 for container 10 to stand unassisted on flat surfaces.

Figure 3:
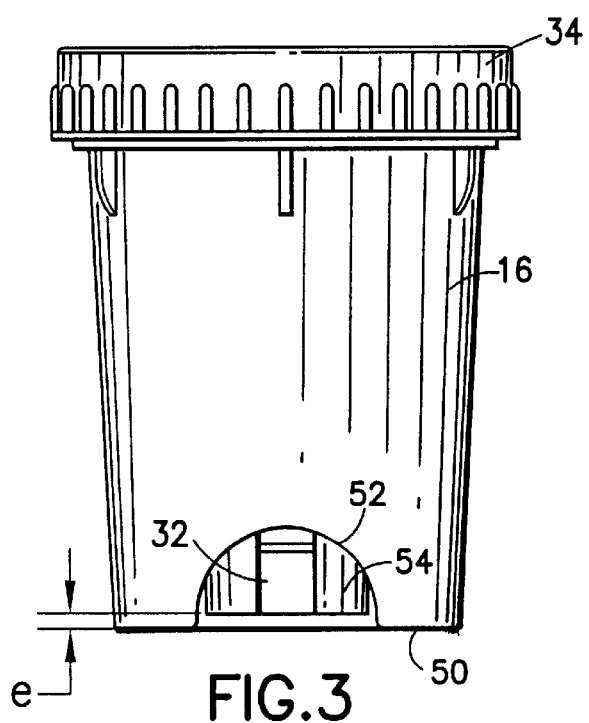
FIG. 3 is a side view of the collection container shown in FIG. 1.
Figure 4:
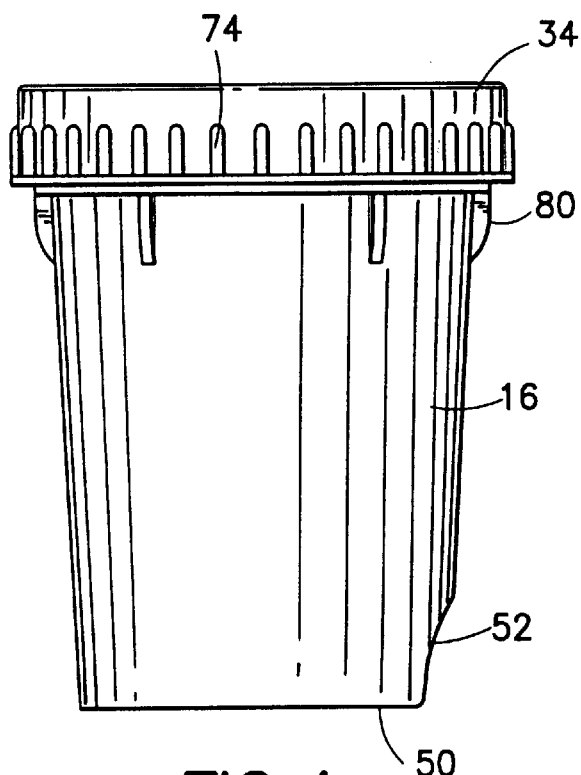
FIG. 4 is a front view of the collection container shown in FIG. 1.

Circular extension portion 44 is characterized by having a hemispherical recess 52 as shown in FIG. 3. Hemispherical recess 52 allows access to integrated valve 32.

Bottom 12 is further characterized by comprising an annular protective flap 54 surrounding valve 32. Annular protective flap 54 is preferably a semi-circular ledge. The function of flap 54 is to reduce potential splatter from valve 32 when valve 32 is pierced. Flap 54 also functions by securing the transfer container to valve 32. Preferably, container 10 has circular extension portion 44 and flap 54 as a unitary structure with bottom 12. However, flap 54 and circular extension portion 44 may be separate components attached to bottom 12 by various methods known in the art.

Annular protective flap 54 is further characterized by being recessed within circular extension portion 44 as shown in FIG. 3. A recessed distance "e" is measured from planar bottom 50 of extension portion 44 to the bottom of flap 54. Distance "e" allows further protection of exposure to the specimen from integrated valve 32. It also protects valve 32 when container 10 is placed on flat surfaces.

Side walls 16 is further characterized by including at least one external protrusion 60. Lid 34 is further characterized by having at least one internal protrusion 62. External protrusion 60 and internal protrusion 62 mate together such that when lid 34 is connected by internal protrusion 62 to external protrusion 60 a permanent and leak-resistant connection is formed between lid 34 and side walls 16. This permanent and leak-resistant connection allows container 10 to be transported by itself without transfer to another container for transport. Preferably, external protrusion 60 and internal protrusion 62 are threads as shown in FIGS. 1 and 7. However, other attachment structures could be provided, such as an annular groove, an annular rim, or spaced-apart dimples.

Internal protrusion 62 is further characterized by having a crimp area 112. Crimp area 112 provides the permanent and leak-resistant connection between lid 34 and side walls 16 by constricting external protrusions 60 on side walls 16. The deformation that occurs to external protrusion 60 enables the permanent connection to be formed and lid 34 unable to be removed after tightened. Crimp area 112 is formed by internal protrusion 62. Internal protrusion 62 narrows to a width smaller than the width of external protrusion 60 thereby forming crimp area 112.

Integrated valve 32 is further characterized by including a conical inlet 72. The function of the conical inlet 72 is to provide an audible and tactile confirmation of the opening of valve 32 when pierced.

Lid 34 further include an array of ribs 74. Side walls 16 further include an array of ribs 80. Array of ribs 74 and ribs 80 assist in gripping lid 34 and side wall 16 during the locking of both components.

If the medical technidan determines not to transport collection container 10 to a laboratory for analysis, transfer of the specimen from collection container 10 to a test tube 82 is provided. Test tube 82 comprises a closed bottom 84 an open top 90 and a stopper 94. A plurality of cylindrical side walls 92 extend between closed bottom 84 and open top 90. Stopper 94 has a stopper cover 96 that is attached to stopper 94 by a hinge 98.

Figure 8:
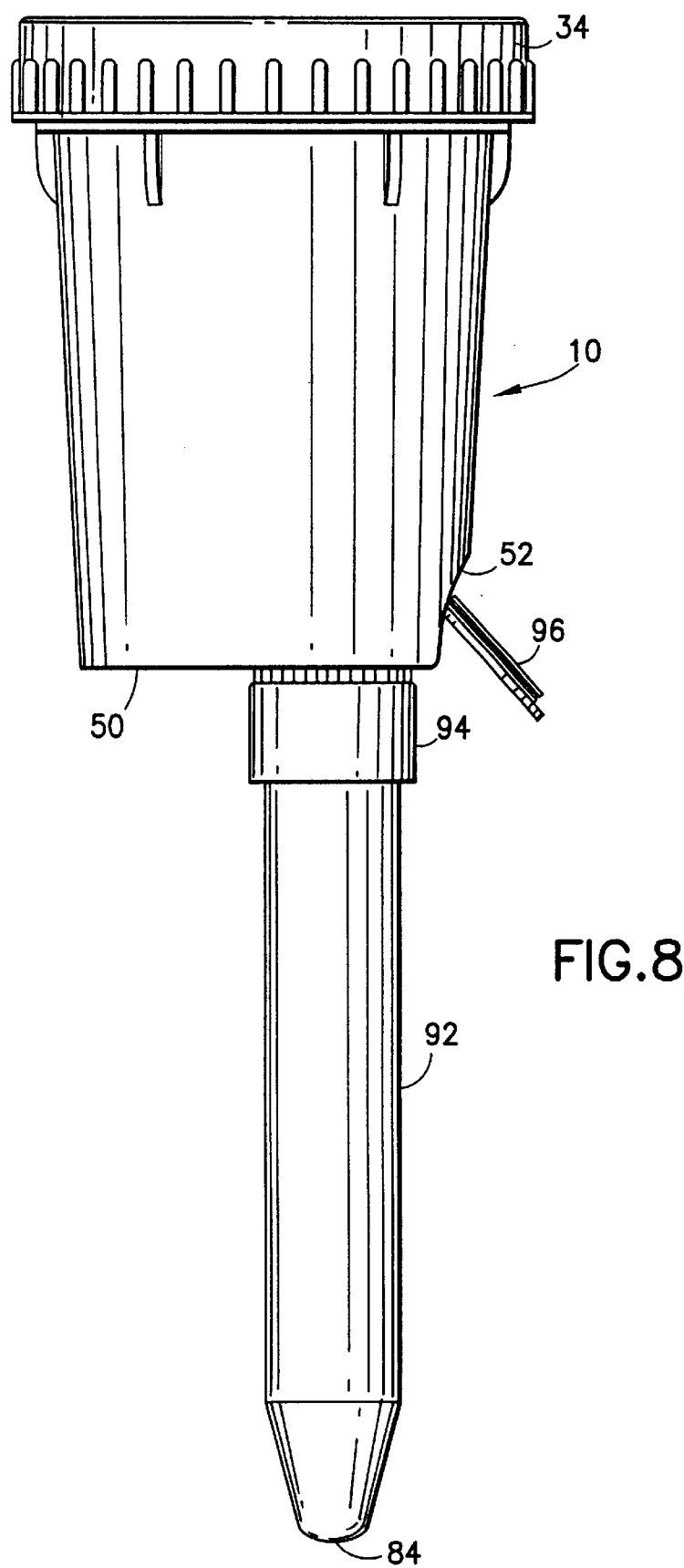
FIG. 8 is a side view of the container and tube assembly.
Figure 9:
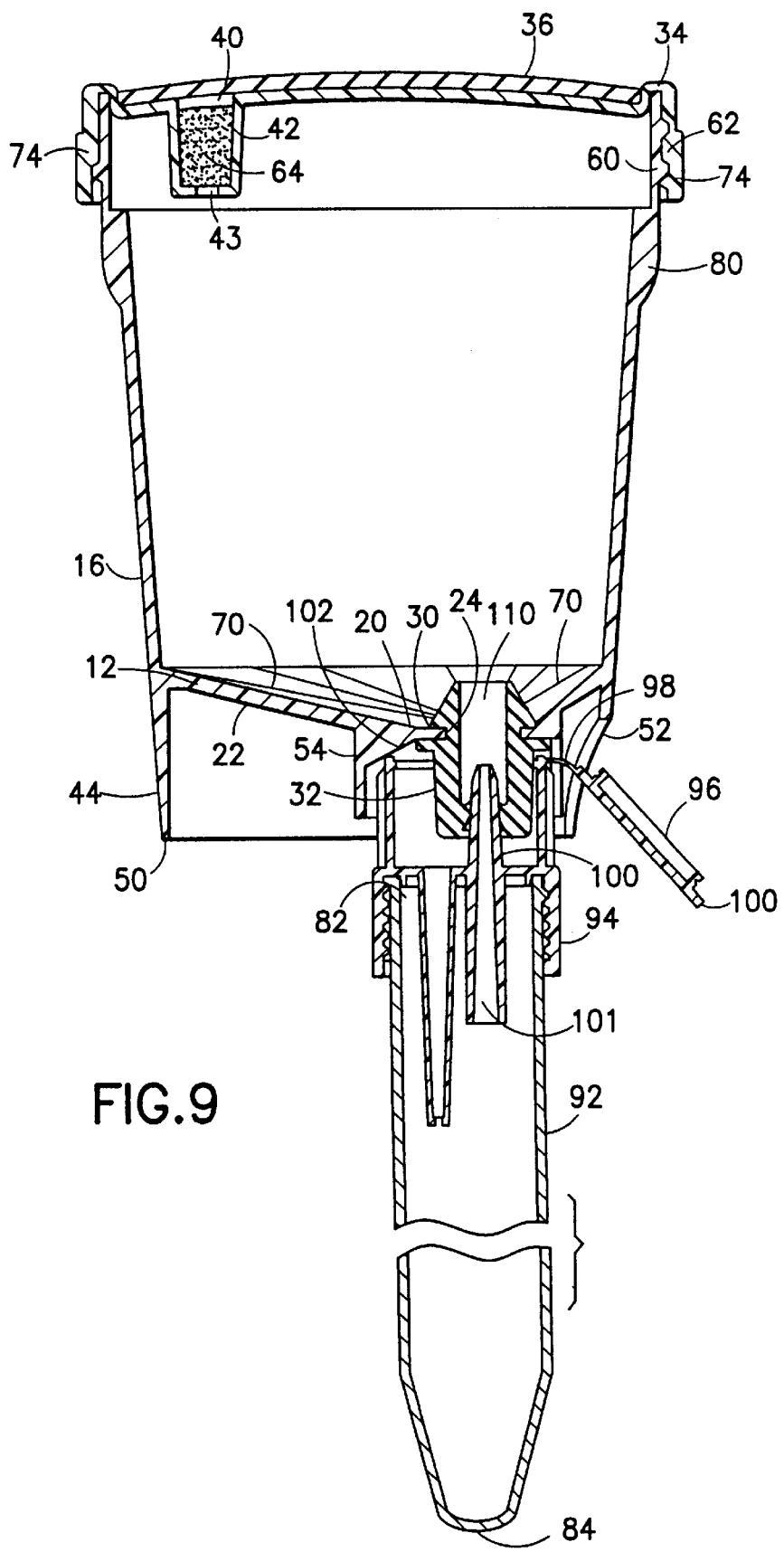
FIG. 9 is a cross-sectional view of FIG. 8.

Stopper 94 is characterized by having a piercing member 100 for attaching test tube 82 into integrated valve 32 such that container 10 is in fluid communication with test tube 82. Piercing member 100 has a channel 101 therethrough to provide for the fluid communication. Preferably, piercing member 100 is a blunt cannula or tube. Attachment of test tube 82 to container 10 is shown in FIGS. 7–9. Stopper 94 is attached to open top 14. Preferably, an array of external threads are on test tube 82 to attach with stopper 94. However, other attachment structures could be provided. Such attachment structures include but are not limited to snap fits, mechanical fasteners, spaced-apart dimples, and annular rims.

Circular top surface 20 is preferably circular to allow maximum flow of the specimen toward aperture 24 in integrated valve 32. Other such shapes for top surface 20 include, but are not limited to, rectangular shapes, triangular shapes and elliptical shapes. Grooves 70 would also assist in maximizing the flow of the specimen toward aperture 24 for these shapes as it does for circular top surface 20.

Valve 32 is preferably a separate component from bottom 12. Preferably, valve 32 is made of an elastomeric material. Such elastomeric materials include, but are not limited to, styrene butadiene copolymers, thermoplastic rubbers, isoprene, EPDM, olefin-based elastomers, acrylic-based elastomers, polyurethane, and silicone-based elastomers. Valve 32 is a self-sealing valve. Once piercing member 100 is removed, valve 32 self seals and closes automatically stopping the transfer of specimen.

External protrusions 60 and internal protrusion 62 are characterized by providing side walls 16 with a permanent and leak-resistant connection to lid 34. This permanent and leak-resistant seal allows the closed system specimen collection container 10 to be transported to the laboratory for analysis rather than test tube 82. However, it is within the purview of this invention that a medical technician can transfer the fluid specimen from collection container 10 into test tube 82 and then transport test tube 82 to a laboratory for further analysis.

Operation of closed system specimen collection container 10 begins with having lid 34 off open top 14. The specimen is collected in container 10 and lid 34 is tightened over open top 14. Lid 34 makes a permanent and leak-resistant seal with side walls 16 via crimp area 112. At this point, container 10 can be shipped to a laboratory for analysis because of the permanent and leak-resistant seal formed by lid 34 and side walls 16. However, the medical technician may decide to transfer the liquid specimen from container 10 into test tube 82.

For transferring the specimen into test tube 82, piercing member 100 pierces integrated valve 32. Piercing member 100 goes through a distal valve opening 106 and pierces the integrated valve 32. A plurality of supporting ribs 102 assist in resisting deformation of integrated valve 32 as to prevent any leakage from such a deformation. Flap 54 assists in protecting from any splatter during piercing. In addition, flap 54 provides additional holding to stopper 94 when piercing member 100 enters integrated valve 32. The fluid specimen is guided by grooves 70 on circular top surface 20 where the fluid enters a proximal valve opening 110. Fluid then flows through proximal valve opening 110 to distal valve opening 106 and through channel 101 of piercing member 100. Fluid then enters test tube 82 to the desired volume. The desired volume of specimen transferred is determined by the volume available in test tube 82. Once the volume is filled, transfer of the specimen automatically stops. Piercing member 100 is removed when the desired volume is achieved. Integrated valve 32 self-seals such that no additional fluid is transferred from integrated valve 32 when piercing member 100 is removed. Thus, no mechanical turning or manipulation is required by the medical technician to put integrated valve 32 in the closed position so that fluid stops transferring out of integrated valve 32 from container 10. Integrated valve 32 simply self-seals when piercing member 100 is removed. Thus, no leaks occur when piercing member 100 is removed because of the self-sealing property of valve 32.

When the desired volume has been transferred into test tube 82, stopper cover 96 is rotated to cover stopper 94. At this point, test tube 82 is ready to be transported to a laboratory for further analysis. If multiple samples are desired to be transferred from container 10, the above procedure is repeated using another test tube containing the piercing member.

The embodiment depicted in FIGS. 1–9 are intended to be merely exemplary, and are not intended to depict all possible embodiments of the present invention. Rather, closed system specimen collection container 10 can be any shape that allows a permanent and leak-resistant seal by lid 34 so that container 10 can be transported to a laboratory for analysis. In addition, the present invention enables the specimen to be transferred to test tube 82 and provides safety from spills or leakages via self-sealing integrated valve 32. Valve 32 requires no manual manipulation to close. Valve 32 is closed simply by removing piercing member 100 which is connected to stopper 94 of test tube 82. Thus, the present invention provides safe and easy-to-use components in the transfer and transport of specimens from closed system specimen collection container 10.

What is claimed is:

1. A closed system specimen collection container comprising:

a container comprising a bottom, an open top, and side walls extending from said bottom to said open top, said bottom comprising a center point, an integrated valve a circular top surface and a bottom surface, said top surface inclined and having an aperture located at a point that is the lowest gravitational point on said top surface; said integrated valve protruding from said bottom surface and offset from the center point of said bottom, said valve in fluid communication with said aperture and allowing multiple sampling such that said valve is opened when said valve is punctured and said valve is closed when the puncture is removed; and a lid disposed around said open top and having a recessed area forming a vent, said vent for allowing air to permeate from said container.

2. The specimen collection container of claim 1, further comprising a circular extension portion connected to said bottom and extending distally downward, said circular extension portion having a substantially planar bottom for said container to stand unassisted on flat surfaces.

3. The specimen collection container of claim 2, wherein said circular extension portion further having a hemispherical recess for allowing access to said valve.

4. The specimen collection container of claim 1, wherein said bottom further comprises an annular protective flap surrounding said valve for reducing splatter when the valve is pierced.

5. The specimen collection container of claim 1, wherein said side walls include at least one external protrusion and said lid includes at least one internal protrusion such that when said lid is connected by said internal protrusion to said external protrusion, a permanent and leak-resistant connection is formed between said lid and said side walls.

6. The specimen collection container of claim 1, wherein said valve includes a conical inlet for providing audible and tactile confirmation of the opening of said valve when pierced.

7. The specimen collection container of claim 1, wherein said side walls and said lid further comprise an array of ribs for gripping said lid during locking of said lid on said side walls.

8. The specimen collection container of claim 1, further comprising a test tube having a closed bottom, an open top, cylindrical side walls extending therebetween, and a stopper attached to said open top, said stopper having a piercing member for attaching said test tube to said valve such that the container is in fluid communication with said test tube.

9. The specimen collection container of claim 1, wherein said vent of said lid is offset from the center point of said lid, and said lid further includes an air-permeable lid cover disposed thereon, said lid cover allows air flow from said membrane.

* * * * *